(12) United States Patent
Yuan et al.

(10) Patent No.: US 11,992,262 B2
(45) Date of Patent: May 28, 2024

(54) ANTI-CONTAMINATION LASER SURGERY DEVICE WITH BUILT-IN OPTICAL ELEMENT

(71) Applicant: PEKING UNIVERSITY SCHOOL OF STOMATOLOGY, Beijing (CN)

(72) Inventors: Fusong Yuan, Beijing (CN); Peijun Lyu, Beijing (CN); Shanshan Liang, Beijing (CN)

(73) Assignee: PEKING UNIVERSITY SCHOOL OF STOMATOLOGY, Beijing (CN)

(*) Notice: Subject to any disclaimer, the term of this patent is extended or adjusted under 35 U.S.C. 154(b) by 406 days.

(21) Appl. No.: 17/489,696

(22) Filed: Sep. 29, 2021

(65) Prior Publication Data
US 2022/0015830 A1 Jan. 20, 2022

Related U.S. Application Data

(63) Continuation of application No. PCT/CN2019/086572, filed on May 13, 2019.

(30) Foreign Application Priority Data

Apr. 8, 2019 (CN) .......................... 201910276778.8

(51) Int. Cl.
*A61B 18/20* (2006.01)
*A61B 34/20* (2016.01)
(Continued)

(52) U.S. Cl.
CPC .............. *A61B 18/20* (2013.01); *A61B 34/20* (2016.02); *G02B 7/02* (2013.01); *G02B 26/0833* (2013.01);
(Continued)

(58) Field of Classification Search
CPC ................... A61B 18/20; A61B 34/20; A61B 2017/00389; A61B 2018/00601; A61B 2018/00827; A61B 2018/20359; A61B 2034/2057; A61B 18/201; A61B 18/22; A61B 2017/00057; A61B 2017/00128; A61B 2018/00017; A61B 2018/00785; A61B 2018/20353; A61B 90/361;
(Continued)

(56) References Cited

U.S. PATENT DOCUMENTS

2006/0269896 A1 11/2006 Liu et al.

FOREIGN PATENT DOCUMENTS

| CN | 102715956 A | 10/2012 |
|---|---|---|
| CN | 105125312 A | 12/2015 |

(Continued)

*Primary Examiner* — Scott M. Getzow (57) ABSTRACT

An anti-contamination laser surgery device with a built-in optical element, including an inner cylinder, an outer cylinder, a first unit configured to enable the inner cylinder and the outer cylinder to be telescopic, a lens moving unit, a two-dimensional laser scanning unit, a real-time monitoring unit, and a second unit configured to perform unidirectional laminar flow ventilation. A head end of the inner cylinder and a tail end of the outer cylinder are matched and connected by the first unit. The two-dimensional laser scanning unit and the real-time monitoring unit are arranged at the head end of the outer cylinder, and the lens moving unit is arranged in the inner cylinder and close to the head end of the inner cylinder. The second unit is arranged close to a tail end of the inner cylinder.

10 Claims, 3 Drawing Sheets

(51) Int. Cl.
  *G02B 7/02*   (2021.01)
  *G02B 26/08*  (2006.01)
  *G02B 26/10*  (2006.01)
  *A61B 17/00*  (2006.01)
  *A61B 18/00*  (2006.01)
  *A61C 1/00*   (2006.01)

(52) U.S. Cl.
  CPC .. *G02B 26/101* (2013.01); *A61B 2017/00389* (2013.01); *A61B 2018/00601* (2013.01); *A61B 2018/00827* (2013.01); *A61B 2018/20359* (2017.05); *A61B 2034/2057* (2016.02); *A61C 1/0046* (2013.01)

(58) Field of Classification Search
  CPC .. A61B 2018/20553; A61B 2018/2227; A61B 2090/3614; G02B 7/02; G02B 26/0833; G02B 26/101; A61C 1/0046
  See application file for complete search history.

(56) References Cited

FOREIGN PATENT DOCUMENTS

| | | |
|---|---|---|
| CN | 107851336 A | 3/2018 |
| CN | 108145309 A | 6/2018 |
| CN | 109124576 A | 1/2019 |
| WO | 2018012862 A1 | 1/2018 |
| WO | 2018154485 A1 | 8/2018 |

ANTI-CONTAMINATION LASER SURGERY DEVICE WITH BUILT-IN OPTICAL ELEMENT

CROSS-REFERENCE TO RELATED APPLICATIONS

This application is a continuation of International Patent Application No. PCT/CN2019/086572, filed on May 13, 2019, which claims the benefit of priority from Chinese Patent Application No. 201910276778.8, filed on Apr. 8, 2019. The content of the aforementioned application, including any intervening amendments thereto, is incorporated herein by reference in its entirety.

TECHNICAL FIELD

This application relates to laser processing, and more particularly to an anti-contamination laser surgery device with a built-in optical element.

BACKGROUND

Dental hard tissue disease is one of the most frequent oral diseases, and mainly includes dental caries (commonly known as cavities and tooth decay), tooth defect, and tooth loss. According to the fourth national oral health epidemiological survey report, the incidence of oral diseases in adults is as high as 95.6%, among which dental hard tissue diseases account for more than 85%.

Tooth preparation is a basic process in the treatment of dental hard tissue diseases and is the most commonly-used clinical operation technique. In the process of the tooth preparation, a high-speed dental grinding tool is held to perform three-dimensional quantitative cutting and formation on dental hard tissues (including physiological and pathological enamel, dentin, and cementum) of the affected tooth in the narrow mouth (with a height of approximately 2-5 mm), so as to remove the diseased tissue on the dental hard tissues, or/and shape the remaining healthy hard tissue into a desired three-dimensional geometric shape.

Clinically, the tooth preparation is completed by a traditional method relying on a hand-held high-speed turbine dental drill or a commercially-available dental laser. Unfortunately, these traditional approaches often struggle with the following defects. First, in the narrow and semi-closed oral cavity (a vertical opening width is 2.5-5.0 cm; and there are perioral muscle pressure and random movement of the jaw), it is difficult to meet the relevant standards mentioned in textbooks and clinical operating specifications only relying on human vision and manual positioning to control the operations, which will result in excessive or insufficient tooth preparation, thereby leading to poor accuracy and low efficiency of the clinical tooth preparation, and even causing iatrogenic damages to gums, lips, cheeks, and tongue mucosa. Second, traditional dental drills will produce sharp noise, which makes patients and doctors uncomfortable. Third, the current laser dental drill is still manually held to cut the tooth tissues (only replacing the mechanical power with laser power), so it also cannot get rid of the limitations of manual operation. Fourth, the commercially-available laser for tooth preparation will cause micro-cracks on the cutting surface, irritate the nerves of the dental pulp, cause uncontrollable cutting accuracy and poor cutting surface smoothness, and damage the healthy tooth tissues.

Currently, the technical level of the clinical manual dental preparation in China is relatively low (according to the estimation of relevant experts, the qualified rate is about 40%), and the traditional training process of "clinical operation skills" is extremely time-consuming (usually 5-10 years), which directly leads to a serious shortage of professional dental medical resources with excellent clinical dental preparation operations. By comparison, the ratio of specialist dentists to oral patients in developed countries such as Europe, America, and Japan is about 1:500-2000, while in China is 1:20,000. The serious shortage of dentists with excellent clinical operation ability is one of the roots causing the great difficulty and high cost of getting oral medical treatment in China. In addition, the traditional manual tooth preparation is difficult to meet the relevant standard proposed by the clinical operating specifications. Therefore, it is urgent to develop a new, automated, and intelligent clinical tooth preparation technology to replace the traditional manual method.

At present, the tooth preparation generally requires a four-handed operation, namely, a patient needs to be treated by one doctor and one nurse, leading to high labor cost.

SUMMARY

An object of the present disclosure is to provide an anti-contamination laser surgery device with a built-in optical element to overcome the defects of high labor cost and low efficiency in the traditional clinical tooth preparation relying on a hand-held high-speed turbine dental drill or a commercially-available dental laser.

Technical solutions of the present disclosure are described as follows.

The present disclosure provides an anti-contamination laser surgery device with a built-in optical element, comprising:
an inner cylinder;
an outer cylinder;
a first unit configured to enable the inner cylinder and the outer cylinder to be telescopic;
a lens moving unit;
a two-dimensional laser scanning unit;
a real-time monitoring unit; and
a second unit configured to perform unidirectional laminar flow ventilation;
wherein a head end of the inner cylinder and a tail end of the outer cylinder are matched and connected by the first unit; the two-dimensional laser scanning unit and the real-time monitoring unit are arranged at the head end of the outer cylinder; the lens moving unit is driven by a driving motor, and is arranged in the inner cylinder and close to the head end of the inner cylinder; and
the second unit is arranged close to a tail end of the inner cylinder; a head end of the outer cylinder is sealed; and the tail end of the inner cylinder is provided with a 45° reflector and a light outlet through hole.

In some embodiments, the two-dimensional laser scanning unit is selected from the group consisting of a two-dimensional micro-electro-mechanical system (MEMS) scanning mirror and an assembly thereof, a two-dimensional scanning galvanometer and an assembly thereof, a two-dimensional ultrasonic oscillator and an assembly thereof, and a piezoelectric ceramic scanning tube and an assembly thereof.

In some embodiments, the tail end of the inner cylinder is provided with a detachable bracket; and the 45° reflector and the light outlet through hole are provided on the detachable bracket.

In some embodiments, the first unit comprises:
a button;
a sliding groove; and
a locking knob;
wherein the button is arranged on an outer side of the inner cylinder; and the sliding groove is arranged on an inner side of the outer cylinder, and is matched with the button;
a plurality of variable-radius arc-shaped surfaces are evenly provided on an inner side of the locking knob; and the inner side of the locking knob is provided with an annular groove; and
the tail end of the outer cylinder is provided with a plurality of elastic sheets that are matched with the plurality of variable-radius arc-shaped surfaces one by one; an inner side of an end of each of the plurality of elastic sheets is fixedly connected to an elastic cushion; and an outer side of the outer cylinder is provided with a buckle matched with the annular groove arranged on the inner side of the locking knob.

In some embodiments, the lens moving unit comprises:
the driving motor fixedly connected to an inner side of the inner cylinder;
a screw rod;
a screw nut;
a holder;
a lens; and
a fixing ring;
wherein one end of the screw rod is fixedly connected to a rotating shaft of the driving motor, and the other end of the screw rod is fixedly connected to the holder through the screw nut; and
the lens is fixed in the holder through the fixing ring; the holder is in sliding fit with a sliding groove arranged on the inner side of the inner cylinder through a button arranged on an outer side of the holder.

In some embodiments, the lens moving unit comprises a permanent magnet, a holder, a lens and a hollow moving coil; the permanent magnet is a part of the inner cylinder; the hollow moving coil is sleeved in the permanent magnet; an outer side of the hollow moving coil is wound with a coil; the holder is arranged on an end of the hollow moving coil; the lens is fixed on the holder; and a sliding key arranged on an outer side of the holder is in sliding fit with a sliding groove arranged on the inner side of the inner cylinder.

In some embodiments, the two-dimensional laser scanning unit is the two-dimensional MEMS scanning mirror or an assembly thereof; and the assembly of the two-dimensional MEMS scanning mirror comprises a two-dimensional MEMS scanning mirror holder and a two-dimensional MEMS scanning mirror;
the two-dimensional MEMS scanning lens holder is fixedly connected to the head end of the outer cylinder; the two-dimensional MEMS scanning mirror is arranged in a 45° inclined hole on the two-dimensional MEMS scanning lens holder; and the outer cylinder is provided with a working laser through hole; and
the two-dimensional MEMS scanning mirror is driven by electrostatic drive, electromagnetic drive, piezoelectric drive, electrothermal drive, or a combination thereof.

In some embodiments, the device further comprises a beam splitter and a beam splitter holder; the beam splitter is arranged in a 45° inclined hole on the beam splitter holder; the beam splitter holder is fixedly connected to the inner side of the outer cylinder; one side of the beam splitter is coated with a working laser antireflection film, and the other side of the beam splitter is coated with an imaging light reflection film; and
the beam splitter holder further comprises a horizontal hole and a vertical hole; and the outer cylinder is provided with an imaging light through hole.

In some embodiments, the real-time monitoring unit is a charge-coupled device (CCD) imaging system, an imaging optical fiber system, or other built-in camera systems.

In some embodiments, the second unit comprises at least one ventilation pipe; and the at least one ventilation pipe is arranged on an outer wall of the inner cylinder between the lens moving unit and the light outlet through hole.

Compared to the prior art, the present disclosure has the following beneficial effects.

In the laser surgery device provided herein, a laser two-dimensional scanning unit and a lens moving unit are provided and cooperated to realize the XYZ three-dimensional control of the working laser spot. Moreover, a unit configured to enable the inner and outer cylinders to be telescopic is provided to enable the surgery device to work at different oral depths. The real-time monitoring unit realizes the real-time monitoring of laser cutting status, so as to achieve the safety control. Through a unit configured to perform unidirectional laminar flow ventilation o control the air to flow unidirectionally (toward the light outlet), it can control the temperature of the cutting area, and does not affect the stability of the optical components of the lens moving unit and the two-dimensional laser scanning unit. And at the same time, it avoids the pollution of the optical components caused by the dust generated during cutting, which solves the problems of low level of tooth preparation and high labor cost caused by the traditional methods relying on hand-held high-speed turbo drills or commercialized dental lasers, and thereby reducing the labor cost of tooth preparation.

Another important feature of the laser surgery device provided herein is that the structure of the device supports the hollow fibers that can transmit ultra-short pulse lasers with high-power and high-repetition-frequency in replacing traditional light guide arms to conduct working lasers. The built-in two-dimensional laser scanning unit with a micro galvanometer replaces the traditional galvanometer optical path, which not only ensures the operating flexibility of the system, but also realizes the miniaturization and miniaturization of the robot used in the narrow cavity working space.

BRIEF DESCRIPTION OF THE DRAWINGS

The drawings described herein are used to promote the understanding of the present disclosure. The embodiments presented in the drawings are merely illustrative, and are not intended to limit the disclosure.

DETAILED DESCRIPTION OF EMBODIMENTS

The features and exemplary embodiments of the present invention will be described in detail below. To make the object, technical solutions, and beneficial effects clearer, the disclosure will be described in detail below with reference to accompanying drawings and embodiments. It should be noted that the embodiments described only to explain the present disclosure, and do not limit the present disclosure.

Furthermore, it should also be noted that the terms "comprise", "include" or any other variants are intended to indicate non-exclusive inclusion so that the processes, methods, items, or equipment comprising a series of elements not only include the listed elements but also include other elements that are not displayed specifically, or include the inherent elements for the above-mentioned processes, methods, items or equipment. If there are no more restrictions, the elements defined by the sentence "including . . . " do not exclude the existence of other same elements in the processes, methods, items, or equipment.

Figure 1:
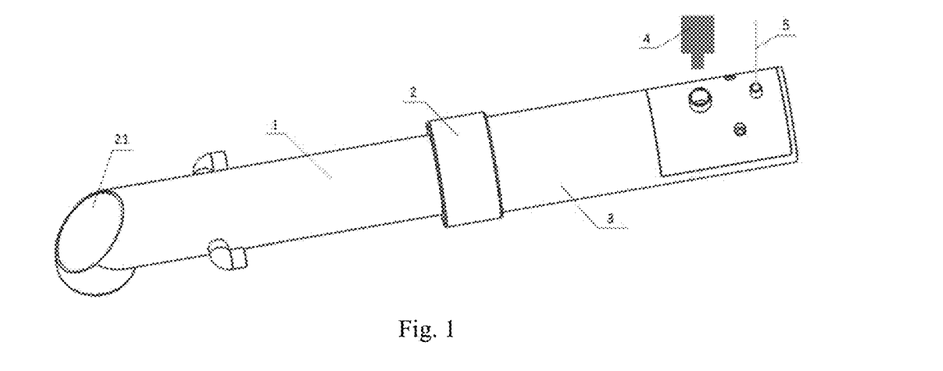
FIG. 1 is a front view of an anti-contamination laser surgery device according to an embodiment of the present disclosure.

Provided herein is an anti-contamination laser surgery device with a built-in optical element. FIG. 1 is a front view of the device according to an embodiment of the present disclosure. The device includes an inner cylinder, an outer cylinder, a first unit configured to enable the inner cylinder and the outer cylinder to be telescopic, a lens moving unit, a two-dimensional laser scanning unit, a real-time monitoring unit and a second unit configured to perform unidirectional laminar flow ventilation. A head end of the inner cylinder and a tail end of the outer cylinder are matched and connected by the first unit. The two-dimensional laser scanning unit and the real-time monitoring unit are arranged at the head end of the outer cylinder. The lens moving unit is driven by a driving motor, and is arranged in the inner cylinder and close to the head end of the inner cylinder. The second unit is arranged close to a tail end of the inner cylinder. A head end of the outer cylinder is sealed. The tail end of the inner cylinder is provided with a 45° reflector and a light outlet through hole.

The device provided in this embodiment can be used for oral dental preparation and other medical fields such as dentistry, orthopedics, dental implantation, ophthalmology, and surgery, or other fields of material processing and molding to complete the removal of hard tissues (tooth, bones), soft tissues or other materials, and can also be used in industrial fields, such as material surface modification and material cutting.

The embodiments of the present invention will be described and illustrated through preferred embodiments.

The laser two-dimensional scanning unit provided herein includes a built-in two-dimensional micro-electro-mechanical system (MEMS) scanning mirror and an assembly thereof. The lens moving unit includes a driving motor, a transmission mechanism, a holder, and a lens. The real-time monitoring unit includes a beam splitter and a CCD imaging system and an assembly thereof. An unit configured to perform unidirectional laminar flow ventilation includes at least one unidirectional ventilation pipe. Through the above design, the laser surgery device achieves a small and compact design. The XYZ three-dimensional control of the working laser spot is realized through the two-dimensional laser scanning unit and the lens moving unit. A unit configured to enable inner and outer cylinders to be telescopic is provided to enable the surgery device to work at different oral depths. Through real-time monitoring, the unit realizes the real-time monitoring of laser cutting dynamics, so as to achieve safety control. Through the unit configured to perform unidirectional laminar flow ventilation to control the air direction to flow unidirectionally (toward the light outlet), it can control the temperature of the cutting area, and does not affect the stability of the optical components of the lens moving unit and the two-dimensional laser scanning unit. And at the same time, it avoids the pollution of the optical components caused by the dust generated during cutting, which solves the problems of the low level of tooth preparation and the high labor cost caused by the traditional methods relying on hand-held high-speed turbo drills or commercialized dental lasers, and thereby reducing the labor cost of tooth preparation.

Another important feature of the laser surgery device provided herein is that the structure of the device supports the hollow fibers that can transmit ultra-short pulse lasers with high-power and high-repetition-frequency in replacing traditional light guide arms to conduct working lasers. The built-in two-dimensional laser scanning unit with a micro galvanometer replaces the traditional galvanometer optical path, which not only ensures the operating flexibility of the system, but also realizes the miniaturization and miniaturization of the robot used in the narrow cavity working space.

To facilitate the high-temperature and high-pressure disinfection of the contaminated front end that may enter the patient or the body, a detachable bracket that can be easily disassembled and separated is provided in this embodiment. The detachable bracket is arranged at the end of the inner cylinder. The detachable bracket includes a 45° reflector and a metal tube wall that can withstand the high-temperature and high-pressure disinfection and has no other sensitive optical elements.

Figure 2A:
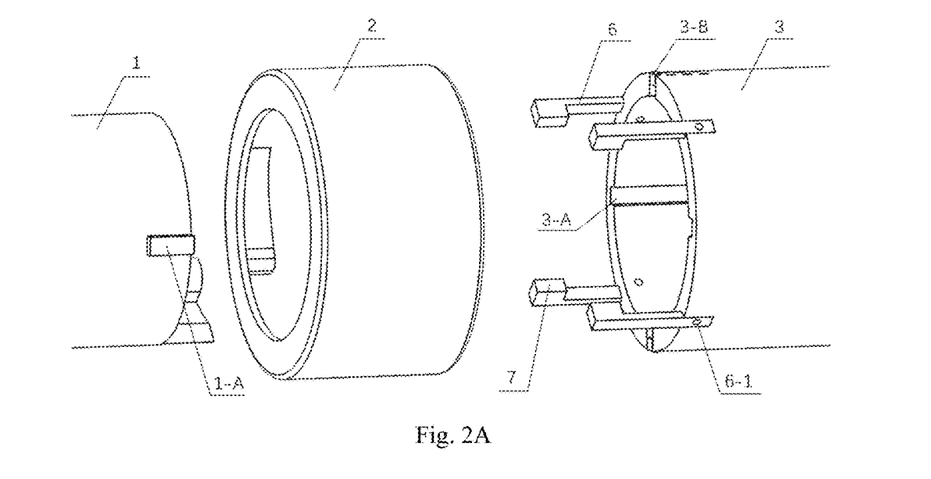
FIG. 2A is an exploded view of a unit for enabling inner and outer cylinders to be telescopic according to an embodiment of the present disclosure.
Figure 2B:
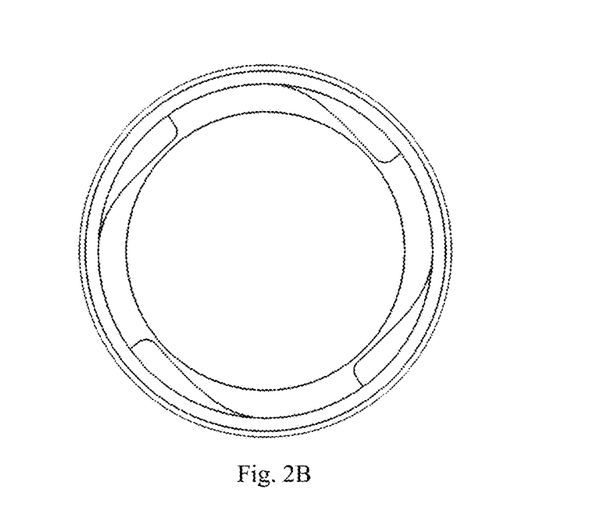
FIG. 2B is a top view of a locking knob according to an embodiment of the present disclosure.
Figure 2C:
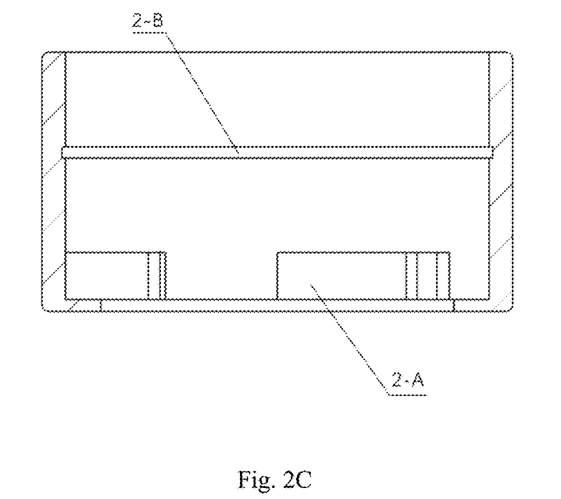
FIG. 2C is a longitudinal sectional view of a locking knob according to an embodiment of the present disclosure.

As shown in FIG. 2A, an exploded view of a unit for enabling inner and outer cylinders to be telescopic is illustrated. The inner cylinder and the outer cylinder have relative sliding, so as to adapt to the working space of different depths. The relative position between the inner cylinder and the outer cylinder is fixed by conveniently locking the inner cylinder through a locking knob. Specifically, the inner cylinder 1 is matched with a sliding groove 3-A arranged on an inner side of the outer cylinder 3 through an inner cylinder key 1-A arranged on an outer side of the inner cylinder 1, so that the inner cylinder 1 can slide relative to the outer cylinder 3 along the sliding groove 3-A. When the relative position between the inner cylinder and the outer cylinder reaches the target position, the locking knob 2 is turned clockwise (or counterclockwise). At this time, a plurality of variable-radius arc-shaped surfaces on an inner surface of the locking knob 2 squeeze the elastic sheets 6 arranged on the tail end of the outer cylinder 3 that are matched with the multiple variable-radius arcs surfaces 2-A one by one, so that an elastic cushion 7 fixedly connected to the inner surface of an end of the elastic sheet 6 will hold the outer surface of the inner cylinder 1. The greater the rotation angle of the locking knob, the greater the deformation of the elastic sheets 6 and the greater the holding force on the outer side of the inner cylinder 1 to lock the inner and outer cylinders. The locking knob 2 is matched with the outer cylinder 3 through a buckle 3-B arranged on the outer side of the outer cylinder 3 and an annular groove 2-B arranged on the inner side of the locking knob 2 so that the axially relative positions between the locking knob 2 and the outer cylinder 3 is fixed. And at the same time, the rotation of the locking knob 2 relatives to the outer cylinder 3 is not restricted. As shown in FIG. 2B-2C, a top view and a longitudinal sectional view of the locking knob are illustrated.

Figure 3:
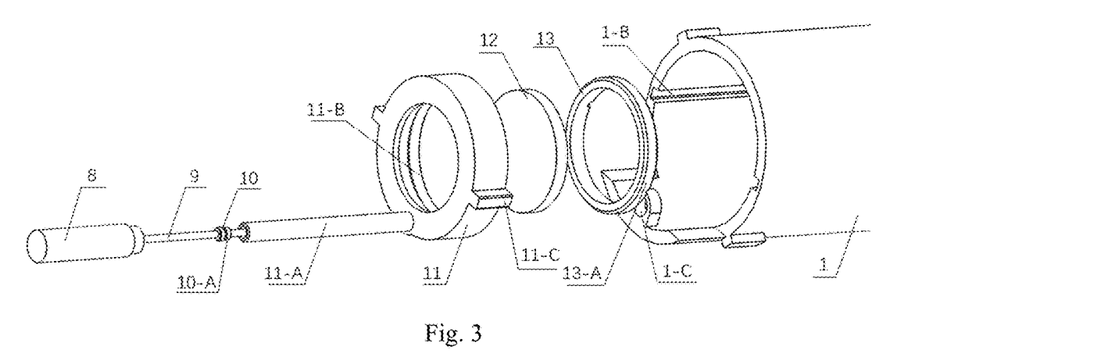
FIG. 3 is an exploded view of a lens moving unit according to an embodiment of the present disclosure.

As shown in FIG. 3, an exploded view of the lens moving unit is illustrated. A small screw nut 10 is matched with a top surface 11-A of the holder 11 through a thread 10-A, so that the holder 11 and the screw 9 are fixedly connected, and the lens 12 is fixed in the holder 11 through the fixing ring 13. The fixing ring 13 is threadedly connected to an inner side 11-B of a bottom of the holder 11 through an outer surface 13-A of the fixing ring 13. The holder 11 is in sliding fit with the slide groove 1-B arranged on the inner side of the inner cylinder 1 through the button 11-C arranged on the outer side of the holder, so that the rotational degree of freedom of the screw nut 10 can be restricted, enabling the holder 11 to slide axially relative to the inner cylinder 1. The driving motor 8 is threadedly connected to a surface 1-C on the inner side of the inner cylinder 1 to be fixedly connected to the inner cylinder 1. The driving motor 8 drives the screw rod 9 to rotate, and then drives the screw nut 10 to move axially by screw driving, thereby driving the holder 11 to slide along the sliding groove 1-B arranged on the inner side of the inner cylinder 1 to realize the movement of the lens. In practical applications, the lens can also be moved by gear transmission, rack and pinion transmission, rope transmission, cam transmission, belt transmission and other transmission methods.

Figure 4:
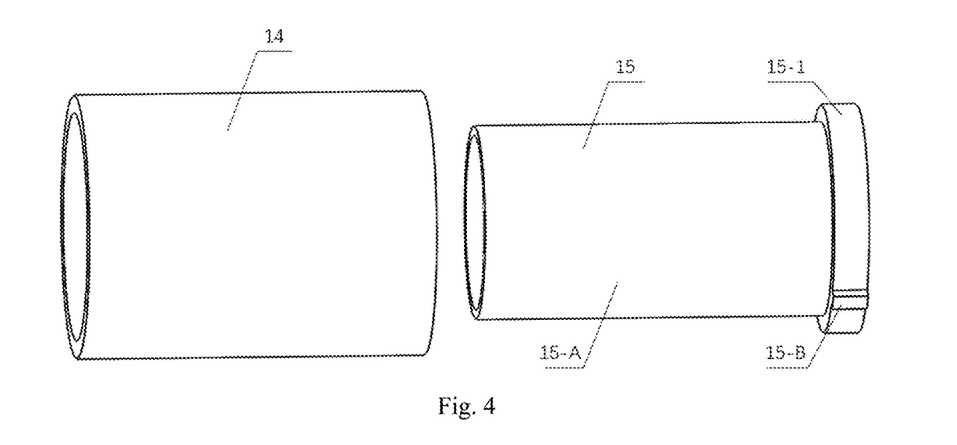
FIG. 4 is an exploded view of a voice coil-type lens moving unit according to an embodiment of the present disclosure.

Another way to realize the movement of the lens is illustrated in FIG. 4. A permanent magnet 14 is a part of the inner cylinder. An outer side 15-A of the hollow moving coil 15 is wound with a coil. The holder 15-1 is integrated with the hollow moving coil 15. A sliding key 15-B arranged on the outer side of the holder 15-1 is in sliding fit with the sliding groove arranged on the inner side of the inner cylinder 1. When the coil is energized, an electromagnetic force is generated in the magnetic field of the permanent magnet, thereby pushing the hollow moving coil 15 and the lens on the holder 15-1 to slide axially along the sliding groove of the inner cylinder 1 relative to the inner cylinder 1.

Figure 5:
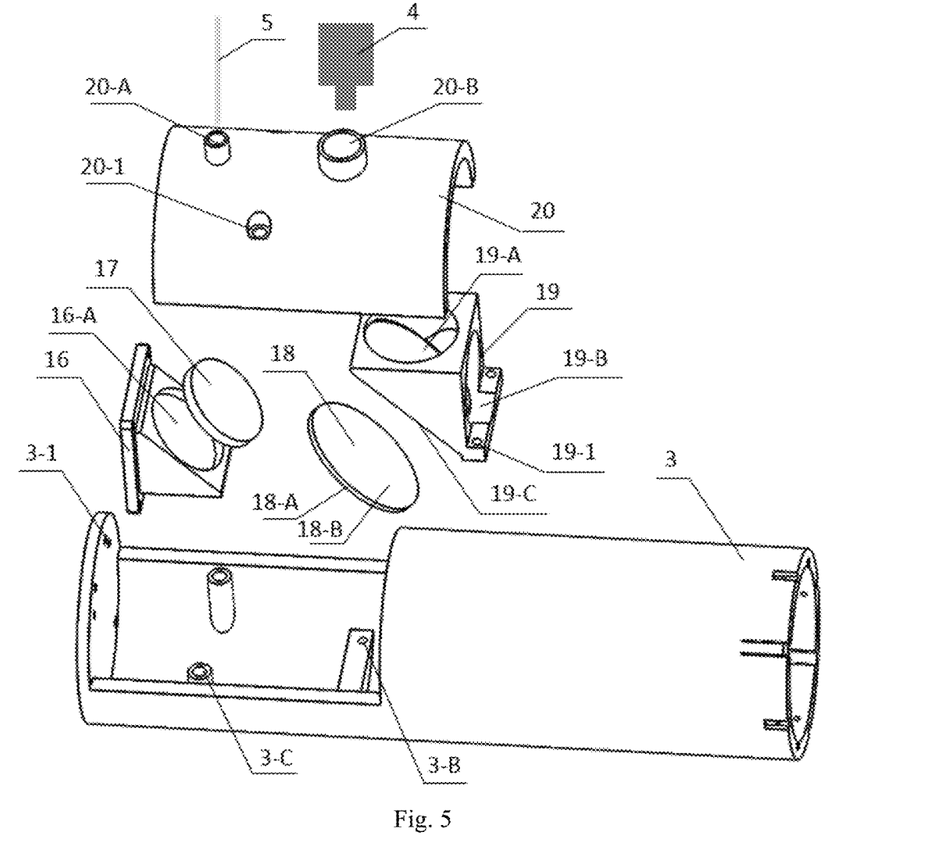
FIG. 5 is an exploded view of a two-dimensional laser scanning unit and a real-time monitoring unit according to an embodiment of the present disclosure.

The two-dimensional laser scanning unit of this embodiment is selected from the group consisting of a two-dimensional MEMS scanning mirror and an assembly thereof, a two-dimensional scanning galvanometer and an assembly thereof, a two-dimensional ultrasonic oscillator and an assembly thereof, and a piezoelectric ceramic scanning tube and an assembly thereof. A two-dimensional scanning unit and a real-time monitoring unit are shown in FIG. 5. The two-dimensional scanning unit includes a two-dimensional MEMS scanning mirror and an assembly thereof. The two-dimensional MEMS scanning mirror assembly includes a two-dimensional MEMS scanning mirror 17 and a two-dimensional MEMS scanning mirror holder 16. The two-dimensional MEMS scanning mirror holder 16 is fixedly connected to the head end of the outer cylinder 3 through a screw 3-1. The scanning mirror 17 is arranged in a hole of the scanning mirror holder 16-A. The two-dimensional MEMS scanning mirror 17 is driven by electrostatic drive, electromagnetic drive, piezoelectric drive, or electrothermal drive. The two-dimensional MEMS scanning mirror 17 realizes the rotation in horizontal and vertical directions, thereby realizing two-dimensional scanning of the incident working laser 5.

In this embodiment, the incident working laser 5 can be directly transmitted to the oscillating mirror of the above-mentioned two-dimensional laser scanning unit through a light guide arm or a dedicated optical fiber (i.e., a hollow fiber).

The beam splitter 18 is arranged in the 45° inclined hole 19-C of the beam splitter holder 19. The beam splitter holder 19 is fixedly connected to the hole 3-B on the inner side of the outer cylinder 3 through a screw 19-1. A first side 18-A of the beam splitter 18 is coated with a working laser anti-reflection film, and a second side 18-B is coated with an imaging light reflection film of a CCD imaging system 4, so that the working laser reflected by the two-dimensional MEMS scanning mirror 17 can pass through the first side 18-A of the beam splitter, and emit through the hole 19-B to be focused by the lens, and finally reflected on the working surface by a 45° reflector 21 at the end of the inner cylinder 1. Moreover, the imaging light of the CCD imaging system 4 (the imaging light can be a working laser or an indicating light source) is reflected by the 45° reflector 21 and the second side 18-B of the beam splitter in sequence, then passes through the hole 19-A, and then enter into the CCD imaging system 4 through the hole 20-B of the outer cylinder 3 to realize the real-time monitoring of the working area. The outer cylinder cover 20 is connected to the outer cylinder hole 3-C by a screw 20-1. In practical applications, the two-dimensional laser scanning can be achieved by using MEMS or piezoelectric ceramic resonance. The working laser can be transmitted through the optical fiber or the light guide arm.

Figure 6:
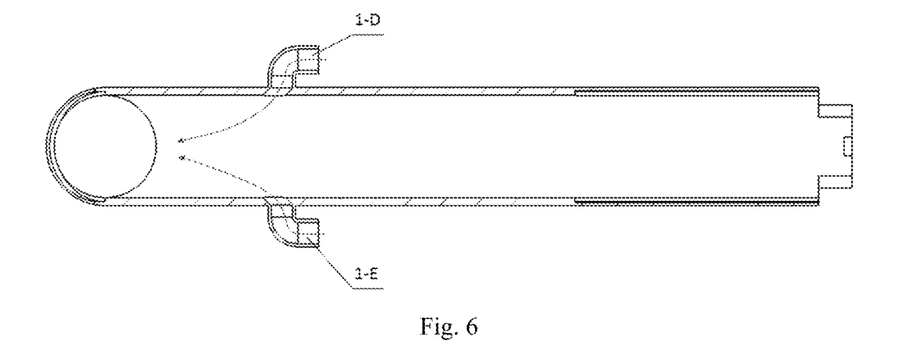
FIG. 6 is a structural diagram of a unit for performing unidirectional laminar flow ventilation according to an embodiment of the present disclosure.

As shown in FIG. 6, a structural diagram of a unit for performing unidirectional laminar flow ventilation is illustrated. Through the design of the direction of ventilation pipes, most of the air flows towards the 45° reflector 21 and the light outlet, forming a positive pressure. The ventilation can remove the dust generated by laser cutting and take away the heat generated by laser cutting. The head end of the outer cylinder is sealed, and basically, no air flows toward the MEMS side, avoiding the influence of ventilation on the stability of the built-in optical components and the contamination caused by cutting dust, oral saliva, bacteria, etc.

It should be noted that the outer shape of the laser surgery device provided herein is a round tube, and it can also be other shapes, such as a square tube. The laser surgery device provided herein is a two-section telescopic shell structure, and based on this, three or more sections of the telescopic shell are all within the protection scope of the embodiment of the present invention. In addition, although the preferred embodiment takes oral tooth preparation as an example to illustrate the laser surgery device, it does not mean that the device can only be applied in oral tooth preparation. For example, the device can also be used in other medical fields such as dentistry, orthopedics, dental implantation, ophthalmology, and surgery, or other fields of material processing and molding, to complete the removal of hard tissue (teeth, bone), soft tissue or other materials, and can also be used in industrial fields, such as material surface modification and material cutting.

In summary, the laser surgery device provided herein is based on built-in MEMS micro-mirrors and movable lenses to realize the miniaturization of the laser surgery device, and integrates the functions of laser cutting and ablation, monitoring, ventilation and dust removal to achieve the fully-automated, intelligent, safe and comfortable dental preparation in clinic. Compared to the manual dental preparation, the laser surgery device provided herein can significantly improve the preparation accuracy, quality and efficiency, and can mitigate the labor intensity of the dentist, eliminating the medical errors caused by human factors. The traditional visual inspection and manual control are replaced with digital measurement and automatic control, so that the "expert-level" clinical operation can be efficiently and repeatedly performed, facilitating enabling the efficient, automatic, precise and intelligent clinical medical treatment. The device of the disclosure enables the intelligent and precise control in the oral clinical treatment, which can alleviate patients' suffering and lower the treatment cost, having a brilliant application prospect.

The above are only preferred embodiments of the present disclosure and are not intended to limit the present disclosure. Any modifications, replacements and improvements made by those skilled in the art without departing from the spirit of the present disclosure shall fall in the scope of the present disclosure defined by the appended claims.

What is claimed is:

1. An anti-contamination laser surgery device with a built-in optical element, comprising:
    an inner cylinder;
    an outer cylinder;
    a first unit configured to enable the inner cylinder and the outer cylinder to be telescopic;
    a lens moving unit;
    a two-dimensional laser scanning unit;
    a real-time monitoring unit; and
    a second unit configured to perform unidirectional laminar flow ventilation;
    wherein a head end of the inner cylinder and a tail end of the outer cylinder are matched and connected by the first unit; the two-dimensional laser scanning unit and the real-time monitoring unit are arranged at the head end of the outer cylinder; the lens moving unit is driven by a driving motor, and is arranged in the inner cylinder and close to the head end of the inner cylinder; and
    the second unit is arranged close to a tail end of the inner cylinder; a head end of the outer cylinder is sealed; and the tail end of the inner cylinder is provided with a 45° reflector and a light outlet through hole.

2. The anti-contamination laser surgery device of claim 1, wherein the two-dimensional laser scanning unit is selected from the group consisting of a two-dimensional micro-electro-mechanical system (MEMS) scanning mirror and an assembly thereof, a two-dimensional scanning galvanometer and an assembly thereof, a two-dimensional ultrasonic oscillator and an assembly thereof, and a piezoelectric ceramic scanning tube and an assembly thereof.

3. The anti-contamination laser surgery device of claim 1, wherein the tail end of the inner cylinder is provided with a detachable bracket; and the 45° reflector and the light outlet through hole are provided on the detachable bracket.

4. The anti-contamination laser surgery device of claim 1, wherein the first unit comprises:
    a button;
    a sliding groove; and
    a locking knob;
    wherein the button is arranged on an outer side of the inner cylinder; and the sliding groove is arranged on an inner side of the outer cylinder, and is matched with the button;
    a plurality of variable-radius arc-shaped surfaces are evenly provided on an inner side of the locking knob; and the inner side of the locking knob is provided with an annular groove; and
    the tail end of the outer cylinder is provided with a plurality of elastic sheets that are matched with the plurality of variable-radius arc-shaped surfaces one by one; an inner side of an end of each of the plurality of elastic sheets is fixedly connected to an elastic cushion; and an outer side of the outer cylinder is provided with a buckle matched with the annular groove on the inner side of the locking knob.

5. The anti-contamination laser surgery device of claim 1, wherein the lens moving unit comprises:
    the drive motor fixedly connected to an inner side of the inner cylinder;
    a screw rod;
    a screw nut;
    a holder;
    a lens; and
    a fixing ring;
    wherein one end of the screw rod is fixedly connected to a rotating shaft of the driving motor, and the other end of the screw rod is fixedly connected to the holder through the screw nut to fixedly connected; and
    the lens is fixedly provided in the holder through the fixing ring; the holder is in sliding fit with a sliding groove arranged on the inner side of the inner cylinder through a button arranged on an outer side of the holder.

6. The anti-contamination laser surgery device of claim 1, wherein the lens moving unit comprises:
    a permanent magnet;
    a holder; a lens; and
    a hollow moving coil;
    wherein the permanent magnet is a part of the inner cylinder; the hollow moving coil is sleevedly provided in the permanent magnet; an outer side of the hollow moving coil is wound with a coil; the holder is arranged on an end of the hollow moving coil; the lens is fixedly provided on the holder; and a sliding key arranged on an outer side of the holder is in sliding fit with a sliding groove arranged on an inner side of the inner cylinder.

7. The anti-contamination laser surgery device of claim 1, wherein the two-dimensional laser scanning unit is an assembly of the two-dimensional MEMS scanning mirror; and the assembly of the two-dimensional MEMS scanning mirror comprises a two-dimensional MEMS scanning mirror holder and a two-dimensional MEMS scanning mirror;
    the two-dimensional MEMS scanning lens holder is fixedly connected to the head end of the outer cylinder; the two-dimensional MEMS scanning mirror is arranged in a 45° inclined hole on the two-dimensional MEMS scanning lens holder; and the outer cylinder is provided with a working laser through hole; and
    the two-dimensional MEMS scanning mirror is driven by electrostatic drive, electromagnetic drive, piezoelectric drive, an electrothermal drive, or a combination thereof.

8. The anti-contamination laser surgery device of claim 7, further comprising:
    a beam splitter; and
    a beam splitter holder;
    wherein the beam splitter is arranged in a 45° inclined hole on the beam splitter holder; the beam splitter holder is fixedly connected to an inner side of the outer cylinder; one side of the beam splitter is coated with a working laser antireflection film, and the other side of the beam splitter is coated with an imaging light reflection film; and the beam splitter holder further comprises a horizontal hole and a vertical hole; and the outer cylinder is provided with an imaging light through hole.

9. The anti-contamination laser surgery device of claim 1, wherein the real-time monitoring unit is a charge-coupled device (CCD) imaging system, an imaging optical fiber system, or other built-in camera systems.

10. The anti-contamination laser surgery device of claim 1, wherein the second unit comprises at least one ventilation pipe; and the at least one ventilation pipe is arranged on an outer wall of the inner cylinder between the lens moving unit and the light outlet through hole.

* * * * *